(12) United States Patent
Leung et al.

(10) Patent No.: US 8,829,239 B2
(45) Date of Patent: Sep. 9, 2014

(54) LITHIUM-BASED METAL ORGANIC FRAMEWORKS

(75) Inventors: Emi Leung, Mannheim (DE); Ulrich Mueller, Neustadt (DE); Gerhard Cox, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 353 days.

(21) Appl. No.: 13/002,612

(22) PCT Filed: Jul. 28, 2009

(86) PCT No.: PCT/EP2009/059716
§ 371 (c)(1),
(2), (4) Date: Jan. 4, 2011

(87) PCT Pub. No.: WO2010/012715
PCT Pub. Date: Feb. 4, 2010

(65) Prior Publication Data
US 2011/0112343 A1 May 12, 2011

(30) Foreign Application Priority Data

Jul. 30, 2008 (EP) .................................... 08161478

(51) Int. Cl.
*C07C 53/08* (2006.01)
*C07C 53/10* (2006.01)
*C07F 1/00* (2006.01)
*C07C 53/06* (2006.01)

(52) U.S. Cl.
CPC ................. *C07F 1/005* (2013.01); *C07C 53/10* (2013.01); *C07C 53/06* (2013.01); *Y02E 60/327* (2013.01); *Y02E 60/328* (2013.01)
USPC ......................................... 562/607; 562/609

(58) Field of Classification Search
CPC ........ C07C 51/418; C07C 53/06; C07C 53/10
See application file for complete search history.

(56) References Cited

U.S. PATENT DOCUMENTS

| 7,556,673 | B2 | 7/2009 | Schubert et al. |
| 2005/0154222 | A1 | 7/2005 | Mueller et al. |
| 2010/0029476 | A1 | 2/2010 | Trukhan et al. |
| 2010/0064888 | A1 | 3/2010 | Schubert et al. |
| 2010/0076220 | A1 | 3/2010 | Schubert et al. |
| 2010/0154635 | A1 | 6/2010 | Schubert et al. |
| 2010/0197990 | A1 | 8/2010 | Schubert et al. |

OTHER PUBLICATIONS

Ferloni et al, Pure & Applied Chemistry, Thermodynamic Properties of Lithium n-Alkanoates, 1992, 64(1), pp. 73-78.*
Rouhi, Chemical and Engineering News, The Right Stuff, 2003, 81(8), pp. 32-35.*
International Search Report issued Oct. 19, 2009 in PCT/EP09/59716 filed Jul. 28, 2009.
Lavalette, Arnaud et al., "Channel Structures in a simple Inorganic Salt—An Open Framework Formed through Structural Integration of Distinct Sodium Acetate and Sodium Perchlorate Domains", Eur. J. Inorg. Chem., pp. 3981-3983, (2004).
Hsu, Leh-Yeh et al., "Structures of Two Forms of Sodium Acetate, $Na^+.C_2H_3O_2$", Acta Cryst. C39, pp. 690-694, (1983).
U.S. Appl. No. 12/863,339, filed Jul. 16, 2010, Schubert, et al.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

An object of the present invention relates to a porous metal organic framework comprising at least one first organic compound and ions of at least one metal, with the skeleton of the framework being formed at least partly by the at least one first organic compound coordinating at least partly in a bidentate fashion to at least two ions of the at least one metal, where the at least one metal is lithium and the at least one first compound is derived from formic acid or acetic acid. Also provided a process for preparing the porous metal organic framework and its use for gas storage or separation.

8 Claims, 2 Drawing Sheets

LITHIUM-BASED METAL ORGANIC FRAMEWORKS

The present invention relates to a porous metal organic framework, its preparation and also processes for storing or separating off a gas by means of the framework and its corresponding use.

Materials for the storage or separation of gases are known in the prior art. For example, mention may be made of activated carbon and molecular sieves and also metal organic frameworks.

Here, the latter metal organic frameworks, make it possible to obtain storage or separation materials which can be used for specific applications by appropriate selection of the metal and of the ligand.

Furthermore, there is, in particular, a need for inexpensive and robust materials which, in particular, display selective behavior in respect of particular gases in storage or separation.

It has been found in the case of metal organic frameworks that it is possible to obtain frameworks whose constituents are known from conventional salts by means of a suitable synthesis.

Thus, for example, a porous metal organic framework which has channels is known from A. Lavalette et al., Eur. J. Inorg. Chem. 2004, 3981-3983. This is a mixed sodium acetate and perchlorate. However, it is emphasized that a template is required for the preparation of a metal organic framework, so that without such a template the pure mixture of sodium acetate and perchlorate results only in formation of hydrated sodium acetate or sodium perchlorate.

In the case of sodium acetate, too, a two-dimensional layer is described by L.-Y. Hsu et al., Acta Crystallogr., Sect. C 1983, 39, 690-694, where the framework is formed by six-fold coordination of sodium ions onto a bidentate acetate and four monodentate acetate groups.

Figure 1:
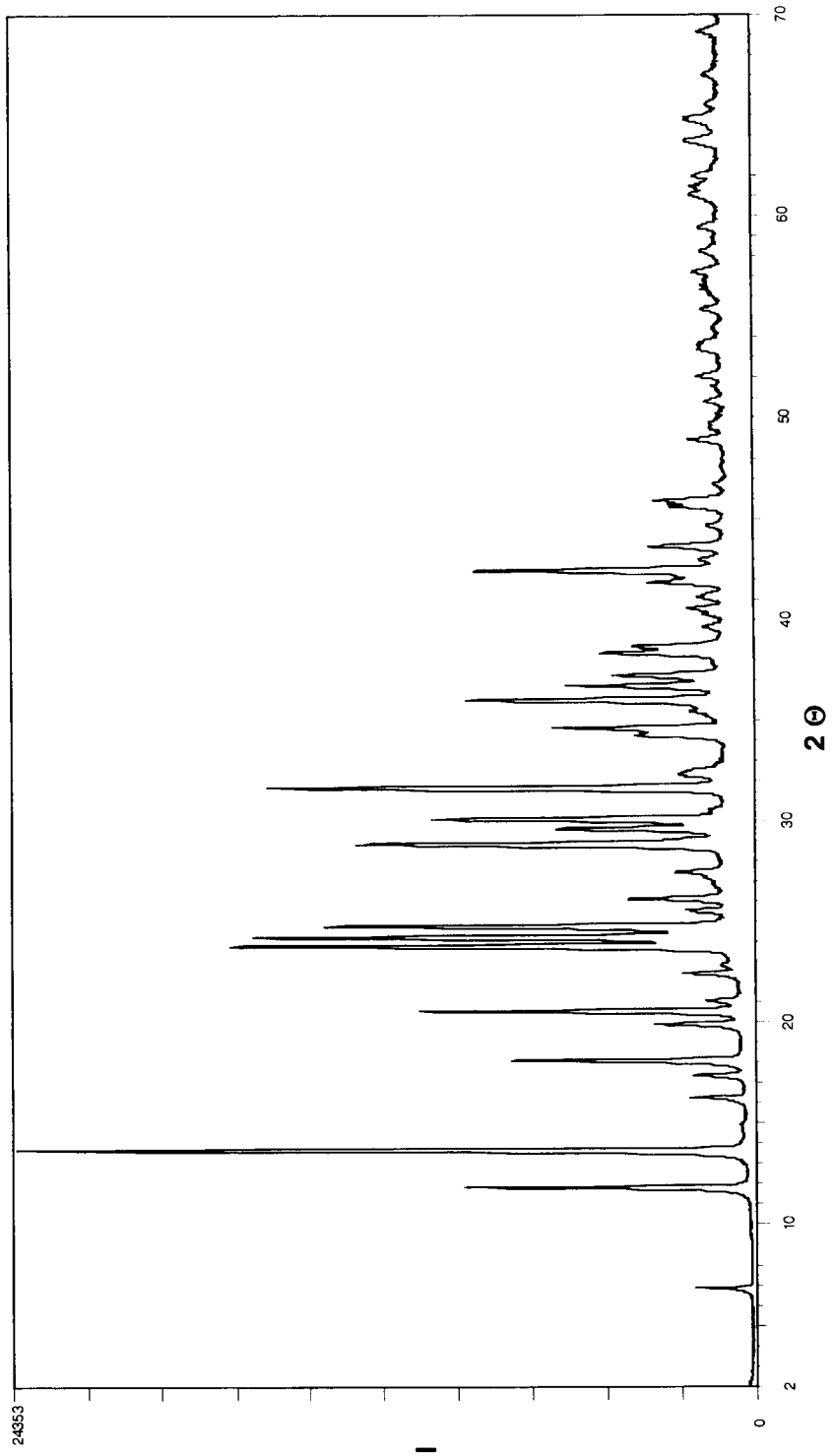
FIG. 1 shows the X-ray diffraction pattern of the Li formate metal organic framework. In the diffraction pattern, I indicates the intensity ($L_{in}$ (Counts)) and 2θ indicates the theta scale.

Despite the metal organic frameworks known in the prior art, there continues to be a need for metal organic frameworks which, in particular, are distinguished by their behavior in storage or separation of gases.

It is therefore an object of the present invention to provide suitable frameworks.

The object is achieved by a porous metal organic framework comprising at least one first organic compound and ions of at least one metal, with the skeleton of the framework being formed at least partly by the at least one first organic compound coordinating at least partly in a bidentate fashion to at least two ions of the at least one metal, where the at least one metal is lithium and the at least one first compound is derived from formic acid or acetic acid.

It has been found that it is possible to obtain porous metal organic frameworks as described above which, owing to their small specific surface area and pore structure, are suitable for gas adsorption and separation and in particular for the storage and selective separation of gases which have small atoms or small molecules.

For the purposes of the present invention, the term "derived" means that formic acid and/or acetic acid are present as formate or acetate in the porous metal organic framework according to the present invention, with the partial presence of a protonated form also being possible.

The porous metal organic framework of the invention thus has a skeleton which is made up at least partly of ions of at least one metal and at least one first organic compound, with the at least one first organic compound being bonded at least partly to two different metal ions, so that a bridging structure to form the framework is made possible. The two ions of the at least one metal can thus be ions of one metal or of different metals, as long as the framework has a plurality of different metals.

However, at least lithium ions have to be present. Preference is given to no further metal ions in addition to lithium ions participating in formation of the framework.

The at least one first organic compound can be derived from formic acid or acetic acid.

The porous metal organic framework of the invention can thus be formate-based or acetate-based.

However, it is also possible for a further organic compound to be present in addition to the first organic compound, with the at least one first organic compound being derived from formic acid and the at least one second organic compound being derived from acetic acid. The porous metal organic framework of the invention is then based on a mixed skeleton comprising formate and acetate.

Particular preference is given to no further organic compound apart from formic acid participating in framework formation in the porous metal organic framework of the invention.

Furthermore, particular preference is given to a porous metal organic framework which comprises no further organic compound apart from acetic acid.

Finally, preference is likewise given to no further organic compound participating in framework formation apart from formic acid and acetic acid.

Very particular preference is given to porous frameworks according to the invention in which the skeleton is made up exclusively of $Li^+$ and formate, $Li^+$ and acetate or $Li^+$, formate and acetate.

If both a first organic compound and a second organic compound are present in the framework of the invention, various molar ratios of first and second organic compounds can occur.

The molar ratio of first organic compound to second organic compound in the metal organic framework of the invention is preferably in the range from 10:1 to 1:10. The ratio is more preferably in the range from 5:1 to 1:5, even more preferably in the range from 2:1 to 1:2, even more preferably in the range from 1.5:1 to 1:1.5, even more preferably in the range from 1.2:1 to 1:1.2, even more preferably in the range from 1.1:1 to 1:1.1 and in particular 1:1. The amounts of formic acid and acetic acid required to achieve the desired ratio can be used in the preparation.

The present invention further provides a process for preparing a porous metal organic framework according to the invention, which comprises the steps (a) reaction of a reaction solution comprising lithium nitrate, formic acid and/or acetic acid and also a solvent at a temperature in the range from 110° C. to 150° C. for at least one day and (b) isolation of the precipitated solid.

The process of the invention for preparing the framework of the invention comprises, as step (a), reaction of a reaction solution comprising lithium nitrate, formic acid and/or acetic acid and also a solvent at a temperature in the range from 110° C. to 150° C. for at least one day.

The reaction is preferably carried out for at least part of the time, in particular at the beginning of the reaction, with stirring. This applies particularly when relatively large amounts are to be reacted.

Lithium nitrate is used as one starting compound. Its initial concentration in the reaction solution is preferably in the range from 0.01 mol/l to 10 mol/l. The initial concentration is more preferably in the range from 0.1 mol/l to 5 mol/l. The initial concentration is more preferably in the range from 0.2 mol/l to 2.5 mol/l. In particular, the initial concentration is in the range from 0.3 mol/l to 1 mol/l.

The lithium nitrate is introduced into the reaction solution in such an amount that the lithium concentration in the reaction solution decreases as a result of the precipitated solid in step (a).

Furthermore, it is preferred that the ratio of the initial molar amount of formic acid used or acetic acid used to the initial molar amount of lithium nitrate is in the range from 1:1 to 3:1. The ratio is more preferably in the region of 1.25:2, more preferably in the range from 1.4:1 to 1.6:1. If formic acid and acetic acid are present, these ratios accordingly apply to the sum of the initial molar amounts of formic acid and acetic acid.

The reaction solution for step (a) of the process of the invention for preparing the metal organic framework of the invention further comprises a solvent in addition to lithium nitrate and formic acid and/or acetic acid.

The solvent should be suitable for bringing the starting materials used at least partly into solution. Furthermore, the solvent should be selected so that operation in the required temperature range is possible.

The reaction in the process of the invention for preparing the material of the invention is thus carried out in the presence of a solvent. It is possible to use solvothermal conditions here. For the purposes of the present invention, the term "thermal" refers to a preparative process in which the reaction is carried out in a pressure vessel which is closed during the reaction and at elevated temperature so that a pressure is built up within the reaction medium in the pressure vessel as a result of the vapor pressure of the solvent present. In this way, the desired reaction temperature can be achieved, if appropriate.

The reaction is preferably not carried out in a medium comprising water. Accordingly, the reaction in the process of the invention is preferably carried out in the presence of a nonaqueous solvent.

The reaction can, for example, be carried out at a pressure of not more than 2 bar (absolute). If the reaction is not carried out under solvothermal conditions, the pressure is preferably not more than 1230 mbar (absolute). The reaction then particularly preferably takes place at atmospheric pressure. However, slightly superatmospheric or subatmospheric pressures can occur as a result of the apparatus. For this reason, the term "atmospheric pressure" refers, for the purposes of the present invention, to a pressure range corresponding to the actual atmospheric pressure ±150 mbar.

The reaction takes place in a temperature range from 110° C. to 150° C. The temperature is preferably in the range from 115° C. to 130° C. The temperature is more preferably in the range from 120° C. to 125° C.

The reaction solution can further comprise a base. The use of an organic solvent frequently makes it unnecessary to use such a base. Nevertheless, the solvent for the process of the invention can be selected so that it itself has a basic reaction, but this is not absolutely necessary for carrying out the process of the invention.

A base can likewise be used. However, preference is given to not using any additional base.

Furthermore, it is advantageous for the reaction to be able to take place with stirring, which is also advantageous in the case of a scale-up.

The (nonaqueous) organic solvent is preferably a $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cyclic ketones such as cyclohexanone, sulfolene or mixtures thereof.

A $C_{1-6}$-alkanol is an alcohol having from 1 to 6 carbon atoms. Examples are methanol, ethanol, n-propanol, i-propanol, n-butanol, i-butanol, t-butanol, pentanol, hexanol and mixtures thereof.

An optionally halogenated $C_{1-200}$-alkane is an alkane which has from 1 to 200 carbon atoms and in which one or more up to all hydrogen atoms can be replaced by halogen, preferably chlorine or fluorine, in particular chlorine. Examples are chloroform, dichloromethane, tetrachloromethane, dichloroethane, hexane, heptane, octane and mixtures thereof.

Preferred solvents are THF, DMF, DEF, DMAc and NMP. Particular preference is given to THF and DMF.

The solvent preferably comprises the abovementioned substances. Further preference is given to using the abovementioned solvents in pure form, i.e. not as mixtures.

The term "nonaqueous" preferably refers to a solvent which does not exceed a maximum water content of 10% by weight, more preferably 5% by weight, even more preferably 1% by weight, more preferably 0.1% by weight, particularly preferably 0.01% by weight, based on the total weight of the solvent.

The maximum water content during the reaction is preferably 10% by weight, more preferably 5% by weight and even more preferably 1% by weight.

The term "solvent" refers to both pure solvents and mixtures of different solvents.

Step (a) of the process of the invention for preparing the framework of the invention is carried out for at least one day. The reaction is preferably carried out for at least 1.5 days, more preferably at least 2 days, more preferably at least 2.5 days, more preferably at least 3 days.

The process of the invention further comprises the step (b), viz. isolation of the precipitated solid.

As a result of step (a) of the preparative process of the invention, the framework precipitates as solid from the reaction solution. It is separated off by methods known in the prior art, e.g. filtration or the like.

The porous metal organic framework of the invention is suitable for storing or separating off a gas.

Accordingly, the present invention further provides a process for storing or separating off a gas, which comprises the step contacting of the gas or a gas mixture comprising the gas with a porous metal organic framework according to the invention.

Accordingly, the present invention also provides for the use of a porous metal organic framework according to the invention for storing or separating off a gas.

The gas adsorption or separation is carried out essentially according to methods known from the prior art.

Principles and industrial processes are described, for example, in Werner Kast, Adsorption aus der Gasphase, VCH Weinheim, 1988.

Pressure swing adsorption is described, for example, in D. M. Ruthwen et al., Wiley-VCH, 1993.

The gas to be adsorbed or separated off can, for example, be hydrogen, natural gas, town gas, hydrocarbons, in particular methane, ethane, ethyne, ethene, propane, n-butane or i-butane, carbon monoxide, carbon dioxide, nitrogen oxides, oxygen, sulfur oxides, halogens, halogenated hydrocarbons, $NF_3$, $SF_6$, ammonia, boranes, phosphanes, hydrogen sulfide, amines, formaldehyde, noble gases, in particular helium, neon, argon, krypton and xenon, nitrogen or oxygen or a mixture thereof.

The gas is preferably selected from the group consisting of nitrogen, hydrogen, oxygen and methane.

EXAMPLES

Example 1

Li Formate Metal Organic Framework from THF

| Starting materials: | 5.3 g of $LiNO_3$ = | 76.9 mmol |
| | 5.3 g of formic acid = | 115.1 mmol |
| Solvent: | 140.0 g of THF = | 1.94 mol |

The lithium nitrate is dissolved in THF in an autoclave liner. The formic acid is added and the solution is stirred for 10 minutes.

Crystallization:
125° C./78 h/static conditions
Work-up:
After cooling, the crystals formed are filtered off and the filtercake is washed 3 times with 50 ml of DMF.
Yield: 3.2 g
Analysis:
Surface area: 20 $m^2$/g determined by the Langmuir method ($N_2$)

FIG. 1 shows the X-ray diffraction pattern of the Li formate metal organic framework according to the invention. In the diffraction pattern, I denotes the intensity ($L_{in}$ (Counts)) and 2 Θ denotes the theta scale.

Example 2

Li Formate Metal Organic Framework from DMF

| Starting materials: | 51.6 g of $LiNO_3$ = | 748.4 mmol |
| | 51.2 g of formic acid = | 1112.32 mmol |
| Solvent: | 516 g of DMF = | 7.1 mol |

Experimental Procedure
a) Synthesis: lithium nitrate is dissolved in DMF under $N_2$ in a 1 l four-neck flask (exothermic to 40° C.). Formic acid is subsequently added carefully (exothermic to 41° C.), the mixture is stirred at room temperature (RT) for 1 hour, then heated to 125° C. in an oil bath and stirred at 125° C. under $N_2$ for 120 hours.
b) Work-up: after cooling to room temperature, the reaction mixture is added to 1.5 l of chloroform, cooled to <10° C. and filtered under $N_2$.
c) Drying: the metal organic framework obtained is sucked dry on a glass frit filter under $N_2$ for 0.5 hour, dried at 60° C. for 2 hours and then dried at 130° C. and 50 mbar in a vacuum drying oven for 8 hours.
Color: Pale pink; yield: 6.8 g
Analysis
Surface area: 2.31 $m^2$/g determined by the Langmuir method ($N_2$)
Elemental analysis: C 21.9%; H 2.1%, O 63%; N 1%; Li 12.7%

Example 3

Li Acetate Metal Organic Framework from DMF

| Starting materials: | 51.6 g of $LiNO_3$ = | 748.4 mmol |
| | 66.8 g of acetic acid = | 1112.32 mmol |
| Solvent: | 516 g of DMF = | 7.1 mol |

Experimental Procedure
The synthesis, work-up and drying are carried out as in example 2.
Color: colorless; yield: 5.2 g
Analysis:
Surface area: 0.175 $m^2$/g determined by the Langmuir method ($N_2$)
Elemental analysis: C 25.2%; H 2.7%; O 57%; N 1.2%, Li 11.9%

Figure 2:
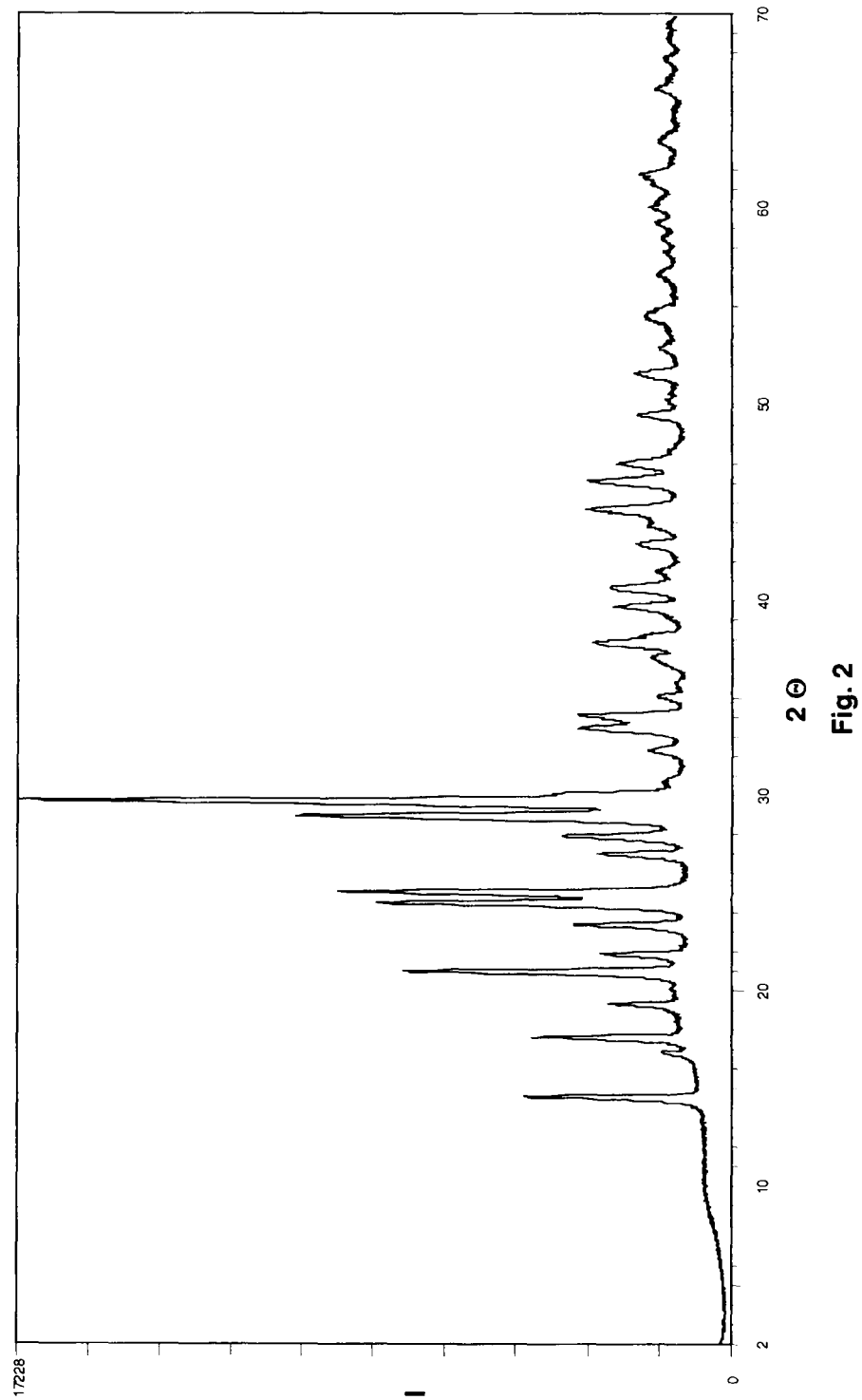
FIG. 2 shows the X-ray diffraction pattern of the Li acetate metal organic framework. In the diffraction pattern, I indicates the intensity ($L_{in}$ (Counts)) and 2θ indicates the theta scale.

FIG. 2 shows the X-ray diffraction pattern of the Li acetate metal organic framework according to the invention. In the diffraction pattern, I denotes the intensity ($L_{in}$ (Counts)) and 2 Θ denotes the theta scale.

The invention claimed is:

1. A porous metal organic framework comprising:
   at least one organic compound selected from the group consisting of formic acid and acetic acid; and
   lithium ions,
   wherein the skeleton of the framework comprises the at least one organic compound coordinated at least partly in a bidentate fashion to at least two lithium ions.

2. The framework according to claim 1, wherein, the framework comprises formic acid and acetic acid coordinated at least partly in a bidentate fashion to the lithium ions.

3. A process for preparing a porous metal organic framework according to claim 1, the process comprising:
   (a) reacting a reaction solution comprising lithium nitrate, formic acid and/or acetic acid, and a solvent at a temperature of from 110° C. to 150° C. for at least one day, and
   (b) isolating a precipitated solid from the reacting.

4. The process according to claim 3, wherein the solvent comprises N,N-dimethylformamide or tetrahydrofuran.

5. A process for storing or separating off a gas, the process comprising:
   contacting the gas or a gas mixture comprising the gas with a porous metal organic framework according to claim 1.

6. The process according to claim 5, wherein the gas is selected from the group consisting of nitrogen, hydrogen, oxygen, and methane.

7. The framework according to claim 1, wherein the at least one organic compound is acetic acid.

8. The framework according to claim 1, wherein the at least one organic compound is formic acid.

* * * * *